US007642082B1

United States Patent
Cao et al.

(10) Patent No.: US 7,642,082 B1
(45) Date of Patent: Jan. 5, 2010

(54) METHODS FOR DETERMINING THE PRESENCE OF STAPHYLOCOCCAL ENTEROTOXIN A GENE IN A SAMPLE

(75) Inventors: Cheng J. Cao, Glen Arm, MD (US); Akbar S. Khan, Joppa, MD (US); Kevin P. O'Connell, Abingdon, MD (US); Jennifer R. Bucher, Joppa, MD (US); Mark V. Gostomski, Bel Air, MD (US); James J. Valdes, Churchville, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 497 days.

(21) Appl. No.: 10/631,224

(22) Filed: Jul. 28, 2003

(51) Int. Cl.
- C12N 1/20 (2006.01)
- G01N 33/569 (2006.01)
- C07H 21/02 (2006.01)

(52) U.S. Cl. .................. 435/252.3; 435/7.33; 536/23.1

(58) Field of Classification Search ............. 435/252.3, 435/7.33; 536/23.1
See application file for complete search history.

(56) References Cited

U.S. PATENT DOCUMENTS

| 5,516,898 | A | 5/1996 | Ohashi et al. |
|---|---|---|---|
| 5,525,718 | A | 6/1996 | Ohashi et al. |
| 5,654,141 | A | 8/1997 | Mariani et al. |
| 2005/0233345 | A1* | 10/2005 | Padmapriya et al. ........... 435/6 |

OTHER PUBLICATIONS

O'Connell et al., 23rd Army Science Conference, Dec. 2002.*
Letertre et al., Molecular and Cellular Probes, vol. 17, pp. 139-147, 2003.*
Borst et al., Infection and Immunity vol. 61, No. 12, pp. 5421-5425, 1993.*
Sequence alignment # STAENAB for SEQ ID No. 3 and SEQ ID No. 5.*
Sequence alignment # AED45640 for SEQ ID No. 1 and SEQ ID No. 2.*

* cited by examiner

Primary Examiner—Robert Mondesi
Assistant Examiner—Khatol Shahnan-Shah
(74) Attorney, Agent, or Firm—Ulysses John Biffoni

(57) ABSTRACT

The present invention relates to methods and assays for determining the presence of staphylococcal enterotoxin A in a sample through detection of a nucleic acid encoding staphylococcal enterotoxin A.

3 Claims, 1 Drawing Sheet

```
tatgctttag aggtgagcaa aatgaaaaaa acagcattta tactactttt attcattgcc    60
ctaacgtgga caacaagtcc acttgtaaat ggtagcgaga aaagcgaaga aataaatgaa   120
aaagatttgc gaaaaaagtc tgaattgcag ggagcagctt taggcaatct taaacaaatc   180
tattattaca atgaaaaaagc taaaactgaa aataaagaga gtcacgatca attttacag   240
catactatat tgtttaaagg ctttttttaca aatcattcat ggtataacga tttattagta   300
gattttgatt caaaggatat tgttgataaa tataaaggga aaaaagtaga cttatatggt   360
gcttattatg gttatcaatg tgcgggtggt acaccaaaca aaacagcttg catgtatggt   420
ggtgtaacgt tacatgataa taatcgattg accgaagaga aaaaagtgcc gatcaattta   480
tggctagacg gtaaacaaaa tacagtacct ttggaaacgg ttaaaacgaa taagaaaaat   540
gtaactgttc aggagttgga tcttcaagca agacgttatt tacaggaaaa atataattta   600
```

FIGURE 1

METHODS FOR DETERMINING THE PRESENCE OF STAPHYLOCOCCAL ENTEROTOXIN A GENE IN A SAMPLE

GOVERNMENTAL INTEREST

The invention described herein may be manufactured, used and licensed by or for the U.S. Government.

FIELD OF THE INVENTION

The present invention is related generally to the detection of biological agents, and more particularly to assays comprising nucleic acid probes and primers, and methods of using the same for detecting nucleic acids associated with encoding or expressing staphylococcal enterotoxin A in a sample.

BACKGROUND OF THE INVENTION

The proliferation of biological weapons and the prospect of terrorism have significantly heightened the need to develop more effective and practical measures for monitoring and detecting biological agents dispersible from such weapons. Such protective measures would be effective for alerting civilian emergency and military personnel of an impending attack and enable those under attack to take necessary defensive actions.

One class of biological agents of concern includes staphylococcal enterotoxins. Staphylococcal enterotoxins are superantigenic protein toxins produced by the bacteria *Staphylococcus aureus* (*S. aureus*). They are generally made up of low molecular weight single-chain proteins (23-29 kDa) subdivided into several serotypes including A, B, C1, C2, C3, D, E, G and H, and which are encoded by five genes which share 50% to 85% homology.

Staphylococcal enterotoxins are the most frequent cause of food poisoning typically resulting in diarrhea and vomiting. In more serious cases, they can trigger toxic shock and immunosuppression. Although high-dose exposures can cause fatalities, it is the incapacitating capability of inhalational exposure on the battlefield or in a populated area that are of most concern in the context of biological defense. In particular, one staphylocbccal enterotoxin that can be readily weaponized is staphylococcal enterotoxin A (SEA). Staphylococcal enterotoxin A, a 27 kDa monomeric protein, is considered to be one of the more potent of the staphylococcal enterotoxin serotypes. Current methods for detecting staphylococcal enterotoxin A are typically time-consuming, labor intensive and unreliable.

Accordingly, there is a need for an assay and a method of detecting the presence of staphylococcal enterotoxin A gene that is relatively fast, accurate and cost effective to implement. There is a further need to develop methods with enhanced sensitivity capable of detecting the presence of genes or nucleic acids encoding staphylococcal enterotoxin A even at low concentration levels. It would be also desirable to develop novel nucleic acid probes and primers useful for detecting nucleic acids, which encode or express staphylococcal enterotoxin A for determining the presence of the toxin itself in a sample.

SUMMARY OF THE INVENTION

The present invention relates to methods for determining the presence of genes or nucleic acids encoding staphylococcal enterotoxin A gene in a sample. The present invention is designed to specifically detect a specific gene or "toxin gene" comprising at least a portion of the nucleic acid which encodes staphylococcal enterotoxin A. The detection of the toxin gene provides a reliable prognosticator of the presence of staphylococcal enterotoxin A in a sample. In a preferred embodiment, the toxin gene is "entA" represented by [SEQ ID NO:8] of Staphylococcal *aureus*.

In one aspect of the present invention there is provided a method of determining the presence of the staphylococcal enterotoxin A (SEA) gene in a sample, comprising contacting a nucleic acid in the sample suspected of emanating from Staphylococcal *aureus*, the nucleic acid including a target nucleic acid sequence encoding staphylococcal enterotoxin A, with a nucleic acid probe capable of selectively hybridizing to at least a portion of the target nucleic acid sequence. In a preferred embodiment, the method further comprises detecting the presence of the target nucleic acid encoding at least a portion of the staphylococcal enterotoxin A as a consequence of the selective hybridization of the nucleic acid probe to the target nucleic acid sequence.

In another aspect of the present invention, there is provided a nucleic acid in the form of a nucleic acid probe suitable for detecting the presence of nucleic acid encoding staphylococcal enterotoxin A (SEA) to determine the presence of staphylococcal enterotoxin A (SEA) in a sample, comprising a nucleic acid sequence selected from [SEQ ID NO:1] and [SEQ ID NO:2].

In another aspect of the present invention, there is provided a nucleic acid in the form of a forward primer for amplifying at least a portion of a target nucleic acid sequence encoding staphylococcal enterotoxin A, comprising a nucleic acid sequence selected from [SEQ ID NO:3] and [SEQ ID NO:4].

In another aspect of the present invention, there is provided a nucleic acid in the form of a reverse primer for amplifying at least a portion of a target nucleic acid sequence encoding staphylococcal enterotoxin A, comprising a nucleic acid sequence selected from [SEQ ID NO:5] and [SEQ ID NO:6]. Each of the reverse primers listed herein operatively correspond as a pair to one of the forward primers described above.

The invention also includes a kit for determining the presence of staphylococcal enterotoxin A (SEA) in a sample via detection of at least a portion of the target nucleic acid sequence encoding staphylococcal enterotoxin A, where the kit comprises a nucleic acid probe component having a nucleic acid sequence selected from [SEQ ID NO:1] and [SEQ ID NO:2] and combinations thereof, a nucleic acid forward primer component having a nucleic acid sequence selected from [SEQ ID NO:3] and [SEQ ID NO:4] and combinations thereof, and a nucleic acid reverse primer component each corresponding to a forward primer and having a nucleic acid sequence selected from [SEQ ID NO:5] and [SEQ ID NO:6] and combinations thereof.

BRIEF DESCRIPTION OF THE DRAWINGS

The following drawings are illustrative of embodiments of the present invention and are not intended to limit the invention as encompassed by the claims forming part of the application.

FIG. 1 depicts a target gene region [SEQ ID NO: 7] of a target nucleic acid sequence of the Staphylococcal *aureus* entA gene [SEQ ID NO: 8] that encodes staphylococcal enterotoxin A wherein sequences indicated by a single line represent preferred forward primers [SEQ ID NO: 3] and [SEQ ID NO: 4], respectively, wherein sequences indicated by double lines represent nucleic acid complements of preferred reverse primers [SEQ ID NO: 5] and [SEQ ID NO: 6], respectively, and wherein sequences indicated by dotted lines represent preferred nucleic acid probes [SEQ ID NO: 1] and SEQ ID NO: 2], respectively, in accordance with the present invention.

DETAILED DESCRIPTION OF THE INVENTION

The present invention relates generally to assays and methods of determining the presence of staphylococcal enterotoxin A in a sample through the detection of a gene encoding staphylococcal enterotoxin A, or the "toxin gene". Preferably, the toxin gene is *Staphylococcus aureus* enterotoxin A gene, or "entA" [SEQ ID NO: 8]. The present invention provides efficient detection of the toxin gene in a manner less prone to error, false positives and background noise through significant reduction of nonspecific amplification or hybridization of a target nucleic acid sequence represented by the toxin gene which encodes staphylococcal enterotoxin A. The present invention is further directed to isolated nucleic acids in the form of primers including forward and reverse primers and further in the form of nucleic acid probes, which have been found to be useful for detecting the toxin gene that may be present in samples. Each of the isolated nucleic acids of the present invention comprise a nucleic acid sequence that is complementary to a portion of the nucleic acid derived specifically from the toxin gene encoding staphylococcal enterotoxin A. The method of the present invention provides sensitive and precise detection in a rapid and cost effective manner.

The term "sample" as used herein means to encompass any sample suspected of containing the biological agent of interest, and includes, but is not limited to, biological samples; body fluids, environmental samples such as air, soil, water, mail, food and the like, laboratory samples, and combinations thereof. The sample may be collected through any suitable collecting means including, but not limited to, wipes, filters, swabs, tubes, vials, and the like.

The term "oligonucleotide" as used herein means a single-stranded nucleotide polymer of greater than 2 nucleotides in length, preferably from about 10 to 100 nucleotides, most preferably from about 12 to 50 nucleotides in length. Such oligonucleotides may be joined by phosphodiester linkages, by phosphorothioate linkages, or by other rare or non-naturally-occurring linkages. Furthermore, an oligonucleotide may have uncommon nucleotides or non-nucleotide moieties. An oligonucleotide as defined herein is a nucleic acid, preferably DNA, but may be RNA or have a combination of ribo- and deoxyribo-nucleotides covalently linked. Nucleic acid probes and primers of a defined sequence may be produced by techniques known to those of ordinary skill in the art, such as by chemical or biochemical synthesis, and by in vitro or in vivo expression from recombinant nucleic acid molecules, e.g., bacterial or retroviral vectors.

The terms "target nucleic acid sequence", "target nucleotide sequence" or "target sequence" encompasses a specific desired deoxyribonucleotide or ribonucleotide sequence comprising all or a part of the nucleotide sequence of a single-stranded target nucleic acid molecule, and the deoxyribonucleotide or ribonucleotide sequence perfectly complementary thereto.

"Stringent" hybridization assay conditions refer to conditions wherein a specific nucleic acid probe is able to hybridize with target nucleic acids (preferably DNA of *S. aureus*) and not to an adverse extent with other nucleic acids present in the sample derived either from other organisms or other sources. It will be appreciated that these conditions may vary depending upon factors including the guanine-cytosine content and length of the probe, the hybridization temperature, the composition of the hybridization reagent or solution, and the degree of hybridization specificity sought. Examples of specific stringent hybridization conditions are provided in the disclosure below.

The term "probe" as used herein means a single-stranded oligonucleotide having a sequence partly or completely complementary to a nucleic acid sequence sought to be detected, so as to stably hybridize thereto under stringent hybridization conditions. In the case of a group or species-specific probe, the probe has the ability to stably hybridize to a target nucleic acid and not to non-target nucleic acids such as those from organisms outside the phylogenetic group or species of interest under stringent hybridization conditions. Probes may, but need not, have regions which are not complementary to a target sequence, as long as such sequences do not substantially alter the probe's desired specificity under stringent hybridization conditions. The probe may be labeled with a reporter group or label moiety such as a radioisotope, a fluorescent or chemiluminescent moiety, with an enzyme or other ligand, which can be used for detection or confirmation that the probe has hybridized to the target sequence.

The present invention is directed to a nucleic acid probe having a nucleic acid sequence selected from a group of specific sequences and that the probe, as a basic and novel characteristic, will form a stable hybrid with a nucleic acid in a nucleotide sequence region having a nucleotide sequence complementary to one of the listed nucleic acid sequences of the group under stringent hybridization conditions. The present invention also encompasses the complement under the corresponding DNA or RNA sequence listed herein.

The term "primer" as used herein means an oligonucleotide capable of hybridizing to a region corresponding to a target nucleic acid sequence thereby acting as a starting site or location for initiating nucleic acid amplification and the term encompasses both the forward and reverse primers. The primer as defined herein is preferably from about 10 to 100 nucleotides in length, and more preferably from about 10 to 50 nucleotides in length.

The term "primer extending reagent" as used herein encompasses any biologically active reagent or macromolecule that is capable of initiating the formation and repair of nucleic acid including extension of polymers or nucleic acids, typically associated with nucleic acid amplification. Typical examples of such reagents include DNA polymerases such as *E. coli* DNA polymerase 1, thermostable DNA polymerase from *Thermus aquaticus* (Taq), and thermostable DNA polymerase from *Bacillus stearothermophilus* (Bst).

The term "nucleic acid hybrid" or "hybrid" as used herein means a nucleic acid structure containing a double-stranded, hydrogen-bonded region, preferably from about 10 to 100 nucleotides in length, most preferably from about 12 to 50 nucleotides in length, wherein each strand is complementary to the other and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

The term "complementary" as used herein means that the nucleotide sequences of similar regions of two single-stranded nucleic acids, or different regions of the same single-stranded nucleic acid have a nucleotide base composition that allows the single strands to hybridize together in a stable double-stranded hydrogen-bonded region under stringent hybridization conditions. When a contiguous sequence of nucleotides of one single stranded region is able to form a series of hydrogen-bonded base pairs with an analogous sequence of nucleotides of the other single-stranded region such that A is paired with U or T, and C is paired with G, the nucleotides sequences are complementary.

The term "nucleic acid amplification" or "target amplification" as used herein means increasing the number of nucleic acid molecules through replication of the desired segment or portion of nucleic acid using techniques as known to a skilled artisan.

Nucleic acid hybridization is the process by which two nucleic acid strands having completely or partially complementary nucleotide sequences come together under predetermined reaction conditions to form a stable, double-stranded hybrid with specific hydrogen bonds. Either nucleic acid strand may be a deoxyribonucleic acid (DNA) or a ribonucleic acid (RNA); thus hybridization can involve RNA:RNA hybrids, DNA:DNA hybrids, or RNA:DNA hybrids.

Thus, as used in this application, the term "hybridization" refers to the ability of two completely or partly complementary single nucleic acid strands to come together to form a stable structure having a double-stranded region. The two constituent strands of this double-stranded structure, or hybrid, are held together with hydrogen bonds. Although these hydrogen bonds most commonly form between nucleotides containing the bases adenine and thymine or uracil (A and T or U) or cytosine and guanine (C and G), base pairing can form between other combinations of bases, who are not members of these "canonical" pairs. Non-canonical base pairing is well-known in the art.

Nucleic acid hybridization is a common method for detecting and quantitating target nucleic acids having specific nucleotide sequences. Such methods are useful for identifying and classifying organisms, diagnosing infectious diseases and genetic abnormalities, testing food and drugs, and identifying criminal suspects, among numerous other things. Typically, nucleic acid hybridization assays use a labeled oligonucleotide hybridization assay probe having a nucleic acid sequence complementary to the target sequence. Such labels are well known in the art, and may include radioactive isotopes, enzymes, or fluorescent, luminescent, or chemiluminescent groups. The probe is mixed with a sample suspected of containing a nucleic acid having the target nucleic acid sequence under hybridization conditions suitable for allowing annealing of the two strands by hydrogen bonding in the region of complementarity. The probe then hybridizes to the target nucleic acid present in the sample. The resulting hybrid duplex may be detected by any suitable technique known in the art.

The term "homologous" refers to the subunit sequence similarity between two polymeric molecules, e.g., between two nucleic acid molecules, two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGCG5' share 50% homology.

In one aspect of the present invention, there is provided a nucleic acid probe having a specific nucleic acid sequence complementary to at least a portion of a target nucleic acid sequence represented by the toxin gene encoding or expressing staphylococcal enterotoxin A. In a preferred embodiment of the present invention, the probe comprises a nucleic acid sequence that is selected from [SEQ ID NO: 1] and [SEQ ID NO: 2].

In another aspect of the present invention there is provided a primer having a nucleic acid sequence complementary to at least a portion of a nucleic acid sequence corresponding to a target nucleic acid sequence associated with a gene encoding or expressing staphylococcal enterotoxin A. In a preferred embodiment of the present invention, the primers typically present in the form of primer pairs including forward primers and reverse primers wherein the forward primers include a nucleic acid sequence that is selected from [SEQ ID NO: 3] and [SEQ ID NO: 4], and wherein the reverse primers may be selected from [SEQ ID NO: 5] and [SEQ ID NO: 6].

In a general aspect of the present invention, the forward and reverse primers and nucleic acid probes are designed to be complementary to specific nucleic acid regions associated with a gene encoding or expressing staphylococcal enterotoxin A, or to an oligonucleotide or nucleic acid comprising a target nucleic acid sequence associated with a gene encoding or expressing staphylococcal enterotoxin A.

The probes of the present invention are designed to hybridize to at least a portion of a target nucleic acid sequence derived from the toxin gene encoding or expressing staphylococcal enterotoxin A under stringent conditions to form hybrids, which would enable specific detection of the target nucleic acid sequence and thus indicate the presence of the toxin, staphylococcal enterotoxin A.

The primers of the present invention are designed and/or selected to hybridize to a nucleic acid sequence, which lies to the 3' side of the portion of a target nucleic acid sequence to be amplified. The hybridized primer prepares the site for nucleic acid amplification to generate a nucleic acid strand complementary to the amplified portion of the target nucleic acid sequence. The newly formed strand also contains the nucleic acid sequence of the amplified portion of the target nucleic acid sequence.

Accordingly, a basic and novel characteristic of the probes and the primers of the present invention is their ability, under appropriate hybridization stringent conditions, to preferentially hybridize to a predetermined region of a target nucleic acid sequence of the toxin gene encoding or expressing staphylococcal enterotoxin A over non-targeted nucleic acids or nucleic acid regions. This specificity is related to the extent of the match between the target nucleic acid sequences and primer or probe involved in the formation of the hybridization complex, and the hybridization stringent conditions.

The present invention further describes double stranded nucleic acid hybrid molecules formed between the probes or primers and their specific target nucleic acid sequences. Hybrids formed between labeled probes and target nucleic acid sequences are useful for the qualitative and/or quantitative detection of a gene encoding or expressing staphylococcal enterotoxin A. These structures may be physically or chemically distinguishable from unhybridized labeled probes after the hybridization reaction based on the label and detection system employed as known to the skilled artisan.

Similarly, the hybrids of the present invention formed between the primers and their complementary nucleic acid regions associated with the target nucleic acid sequence provide an initiation site or at least one cycle of nucleic acid synthesis or replication, reverse transcription and the like. The resulting amplified nucleic acid may then be detected using a probe to form a detectable hybrid molecule. In another embodiment of the present invention, the actual formation of the hybrid molecule produces a detectable event as will be further described hereinafter.

In accordance with the present invention, A first oligonucleotide anneals with a second oligonucleotide with high stringency if the two oligonucleotides anneal under conditions whereby only oligonucleotides which are at least about 70%, and preferably, at least about 90% or, more preferably, at least about 95%, complementary anneal with one another. The stringency of conditions used to anneal two oligonucleotides is a function of, for example, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, Molecular Cloning: A Laboratory Manual, Cold Spring Harbor Laboratory, New York).

Often a sample will not contain a sufficient quantity of nucleic acid molecules to permit direct detection by nucleic acid hybridization due to the sensitivity limits of the particular label used. In such a case, the amount of detectable target nucleotide sequence is increased before nucleic acid hybridization is used for detection. This procedure is termed nucleic acid amplification, and the method of increasing the amount of the target nucleic acid is referred to as amplifying the target nucleic acid or target nucleotide sequence.

In accordance with the present invention, a polymerase chain reaction (PCR) assay adapted for detecting a target nucleic acid sequence of a toxin gene encoding staphylococcal enterotoxin A [SEQ ID NO:8], or at least a portion of a target nucleic acid sequence [SEQ ID NO: 7] which may be used in practicing the present invention for determining the presence of staphylococcal enterotoxin A in a sample. However, the invention should not be construed as being limited to using DNA as a starting point for replication or even to being limited to the particular portion of the gene disclosed. Regardless of the starting point, it is preferred that the target nucleic acid sequence being amplified is unique to the gene for encoding staphylococcal enterotoxin A to the extent that cross-hybridization and/or amplification of other nucleic acids does not appreciably occur. Preferably the target nucleic acid sequence is not present in other related species or in other pathogens. By using a sufficiently unique target nucleic acid sequence, any amplification product produced during the amplification step will not be complementary to and therefore, will not cross-hybridize and/or amplify the nucleic acids of other organisms or sources under high stringency conditions.

Amplification methods involve the use of at least one nucleic acid strand containing a target nucleotide sequence as a template in a nucleic acid polymerizing reaction to produce a complementary second strand containing the target nucleotide sequence. By repeating this process, using the product nucleic acids as templates in subsequent cycles, the number of nucleic acid molecules having the target nucleotide sequence increases rapidly.

Polymerase chain reaction (PCR) methods are the preferred amplification methods used in the amplification step of the present invention. See e.g., Mullis et al., U.S. Pat. No. 4,683,195, the content of which is incorporated herein by reference. However, the amplification step may also be carried out using any suitable amplification technique known in the art or to be developed.

In the preferred PCR amplification procedure used in the present method, a target nucleic acid unique to the gene encoding staphylococcal enderotoxin A is amplified by treating the double-stranded nucleic acid with two nucleic acid primers, each being complementary to one of the two strands of the target nucleic acid. The primers hybridize with their complementary strands and extension products are synthesized using DNA polymerase and at least four deoxyribonucleotide triphosphates (dNTPs). The extension products are separated from their complementary strands by denaturation at an elevated temperature, typically ranging from about 80° C. to 10° C. The reaction mixture is repeatedly cycled between a low temperature annealing step usually ranging from about 37° C. to 70° C. during which the primers hybridize to their complementary strands, an intermediate temperature (from about 70° C. to 80° C.) primer extension step, to the higher temperature denaturation step at a temperature from about 80° C. to 100° C. These temperature steps, collectively referred to as "thermal cycling", are repeated many times, typically about 20 to about 40 cycles are carried out, followed by a final synthesis step at about 70° C. and a 4° C. soak to stop the reaction.

PCR reagents, apart from the target nucleic acid sequence, are needed to perform the PCR process. These PCR reagents generally include five classes of components: (i) an aqueous buffer, (ii) a water soluble magnesium salt, (iii) at least four deoxyribonucleotide triphosphates (dNTPs) (conventionally, dATP, dTTP, dGTP, dCTP), (iv) oligonucleotide primers (typically two primers for each target sequence, the sequences defining the 5' ends of the two complementary strands of the double-stranded target sequence), and (v) a polynucleotide polymerase, preferably a DNA polymerase, more preferably a thermostable DNA polymerase, ie., a DNA polymerase which can tolerate temperatures between 90° C. and 100° C. for a total time of at least 10 minutes without losing more than about half its activity.

Primers for the amplification steps are the same if used for a reverse transcription step at the outset to convert RNA into DNA before carrying out the amplification procedure. Preferably, primers are chosen which only amplify target nucleic acid sequences unique to the gene encoding staphylococcal enterotoxin A. In the present invention, the primers amplify only a corresponding target nucleic acid sequence within the gene encoding staphylococcal enterotoxin A.

Preferred primer pairs and probes target a region of the nucleic acid sequence of the gene encoding staphylococcal enterotoxin A are shown in FIG. 1. Preferred primer pairs including [SEQ ID NO:3] and [SEQ ID NO:5]; and [SEQ ID NO:4] and [SEQ ID NO:6] are used for standard PCR. Each primer set has an internal nucleic acid probe including [SEQ ID NO:1] and [SEQ ID NO:2] which can be used to confirm the identity of the amplification product by PCR amplification.

It will be understood by those skilled in the art that other target nucleic acid sequences specific for the gene encoding staphylococcal enterotoxin A other than the target gene region [SEQ ID NO: 7] as shown in FIG. 1 may be used to specifically identify the staphylococcal enterotoxin A gene in a sample using PCR-based methods, and other similar methods. However, in the present invention, the target nucleic acid sequence and the portion of the amplified target sequence to which the PCR nucleic acid probe hybridizes are sufficiently unique to the staphylococcal enterotoxin A gene that the probe and, primers do not materially hybridize to nucleic acids of other organisms or sources under conditions of high stringency. Thus, the nucleic acid-based detection method of the present invention only detects amplification of the specific, unique target nucleic acid sequence of the staphylococcal enterotoxon A gene and not that of other organisms or sources which may be present in the sample.

In the standard PCR assay, the amplified target nucleic acid sequence can be detected directly by any method that can effectively distinguish the different lengths of DNA. Electrophoresis through agarose gels is the standard method known in the art for use in separating, identifying, and purifying DNA fragments following PCR. The location of the DNA within the gel can be determined directly by staining the gel with low concentrations of the intercalating fluorescent dye, ethidium bromide (EtBr). Band(s) corresponding to the predicted length for the amplified target DNA can then be detected by direct examination of the gel in ultraviolet light.

Additionally, the DNA bands from an electrophoresed sample can be probed by Southern blotting using a single-stranded nucleic acid probe which is complementary to a sequence located between the two selected nucleic acid primers in the amplified target nucleic acid sequence. Usually, the nucleic acid probe is labeled with a radioactive or fluorescent tag, or attached directly or indirectly to an enzyme molecule such that the probe specifically bound to the immobilized complementary target nucleic acid sequence may be localized.

In a preferred embodiment of the present invention, the nucleic acid probe is complementary to at least a portion of the target region [SEQ ID: NO 7] of the toxin gene [SEQ ID NO: 8] encoding staphylococcal enterotoxin A as shown in FIG. 1. However, the present invention is not limited to this sequence or to this gene. Rather, the nucleic acid probe may be selected to hybridize to any amplified target nucleic acid sequence located between two primer pairs all of which hybridize to a sequence in the gene encoding staphylococcal enterotoxin A but which do not materially hybridize to the nucleic acid of any other organism that may be present in the sample of interest so as to adversely affect the qualitative and/or quantitative detection of the target region of the gene [SEQ ID NO: 8] encoding staphylococcal enterotoxin A.

The nucleic acids or oligonucleotides used in the invention may be synthesized by any standard method known or to be developed.

The nucleic acid probes of the present invention are preferably conveniently synthesized on an automated DNA synthesizer such as a Perkin-Elmer Model 392 or 394 DNA/RNA synthesizer available from Perkin-Elmer Inc., Foster City, Calif. using standard chemical methods, such as, for example, phosphoramidite chemistry as known in the art. Alternative chemical methods resulting in non-natural backbone groups, such as phosphorothioate, phosphoramidate, and the like, may also be used provided the hybridization efficiencies of the resulting nucleic acids or oligonucleotides are not adversely affected.

Preferably, the nucleic acid probe is in the range of about 15 to 150 nucleotides in length. The precise sequence and length of a nucleic acid probe of the present invention depends in part on the nature of the target nucleic acid sequence to which it hybridizes. The binding location and length may be varied to achieve appropriate annealing and melting properties for a particular embodiment by one skilled in the art in accordance with known techniques including, but not limited to, "Taq-man"-type assays.

Nucleic acids or oligonucleotides of the present invention include linear oligomers of natural or modified monomers or linkages, such as deoxyribonucleotides, ribonucleotides, and the like, which are capable of specifically binding to a target nucleic acid by way of a regular pattern of monomer-to-monomer interactions, such as Watson-Crick base pairing. Usually, monomers are linked by phosphodiester bonds or their analogs to form oligonucleotides ranging in size from a few monomeric units, e.g., 3 to 4 to several tens of monomeric units. Whenever an oligonucleotide is represented by a sequence of letters, such as "ATGCCTG," it will be understood that the nucleotides are in a 5' to 3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphoranilidate, phosphoramidate, and similar compounds.

In another aspect of the present invention, the nucleic acid probes may further include a reporter and a quencher each attached to the oligonucleotide. During PCR, the modified probe is designed to generate a detectable signal to indicate that it has hybridized with the target nucleic acid sequence. The reporter is a molecule typically a dye which can generate a detectable signal (e.g., fluorescence), and the quencher is a molecule which when placed in close proximity to the reporter is capable of substantially reducing or quenching the intensity of the detectable signal.

As long as both the reporter and the quencher are on the nucleic acid probe, the quencher inhibits the emission of a detectable signal by the reporter. However, as the polymerase extends the primer during amplification, the intrinsic 5' to 3' nuclease activity of the polymerase degrades the probe, separating the reporter from the quencher, and allowing the detectable signal to be emitted. Generally, the amount of detectable signal generated during the amplification cycle is proportional to the amount of product generate in each cycle.

As used herein, the terms "quenching" refer to the process whereby when a reporter and a quencher are in close proximity, and the reporter is excited by an energy source, a substantial portion of the energy of the excited state nonradiatively transfers to the quencher where it either dissipates nonradiatively or is emitted at a different emission wavelength than that of the reporter.

It is well known that the efficiency of quenching is a strong function of the proximity of the reporter and the quencher, i.e., as the two molecules get closer, the quenching efficiency increases. As quenching is strongly dependent on the physical proximity of the reporter and quencher, it has been assumed that the reporter and the quencher be preferably attached to the probe within a few nucleotides of one another, usually with a separation of from about 6 to 16 nucleotides. Typically, this separation is achieved by attaching one member of a reporter-quencher pair to the 5' end of the probe and the other member to a base 6 to 16 nucleotides away.

Preferably, the reporter is selected from fluorescent organic dyes modified with a suitable linking group for attachment to the terminal 3' carbon or terminal 5' carbon of the probe via a linking moiety. The quencher is selected from organic dyes, which may be fluorescent, depending on the embodiment of the present invention. Generally, the absorption band of the quencher should at least substantially overlap the emission band of the reporter to optimize quenching. Non-fluorescent quenchers or dark quenchers typically function by absorbing energy from excited reporters, but do not release the energy radioactively.

Selection of appropriate reporter-quencher pairs for particular probes may be undertaken in accordance with known techniques. Fluorescent and dark quenchers and their relevant optical properties from which exemplary reporter-quencher pairs may be selected are listed and described in, for example, in Berlman, 1971, In: Handbook of Fluorescence Spectra of Aromatic Molecules, 2nd ed., Academic Press, New York. Examples illustrating modifications to reporters and quenchers for covalent attachment via common reactive groups that can be added to an oligonucleotide in the present invention may be found in, e.g., Haugland, 1992, In: Handbook of Fluorescent Probes and Research Chemicals, Molecular Probes, Eugene, Oreg., the content of which is incorporated herein by reference.

Preferred reporter-quencher pairs are xanthene dyes including fluoresceins and rhodamine dyes. Many suitable forms of these compounds are available commercially with substituents on their phenyl groups, which can be used as the site for bonding or as the bonding functionality for attachment to an oligonucleotide. Another preferred group of fluorescent compounds for use as reporters are naphthylamines, having an amino group in the alpha or beta position. Included among such naphthylamino compounds are 1-demethylaminonaphthyl-5 sulfonate, 1-anilino-8-naphthalene sulfonate and 2-p-touidinyl-6-naphthalene sulfonate. Other dyes include 3-phenyl-7-isocyanatocoumarin, acridines, such as 9-isothiocyanatoacridine acridine orange; N-(p-(2-benzoxazolyl)phenyl)maleimide; benzoxadiazoles, stilbenes, pyrenes, and the like.

Most preferably, the reporters and quenchers are selected from fluorescein and rhodamine dyes. These dyes and appropriate linking methodologies for attachment to oligonucleotides are well known in the art.

Suitable examples of quenchers include those selected from 6-carboxy-tetramethylrhodamine, 4-(4-dimethylaminiophenylazo)benzoic acid (DABYL), tetramethylrhodamine (TAMRA), BHQ-0™, BHQ-2™, and BHQ-3™, each of which are available from Bioresearch Technologies, Inc., of Novato, Calif., QSY-7™, QSY-9™, QSY-21™ and QSY-35™, each of which are available from Molecular Probes, Inc., and the like.

Suitable examples of quenchers include those selected from dyes such as SYBR green, 5-carboxyfkluorescein (5-FAM™) available from Applied Biosystems of Foster City, Calif., tetrachloro-6-carboxyfluorescein, 6-carboxy-2'-4,7,7'-tetrachlorofluorescein (6-TET™) available from Applied Biosystems, carboxy-X-rhodamine (ROX), 6-carboxy-4'-5'-dichloro-2',7'-dimethoxyfluorescein (JOE™) available from Applied Biosystems, VIC™ dye products available from Molecular Probes, Inc., NED™ dye products available from Applied Biosystems, and the like.

In one embodiment of the present invention, the probe is attached at the 5' end with a reporter selected from fluoresceins such as 6-carboxyfluorescein (6-FAM) and a quencher selected from rhodamines such as 6-carboxy-tetramethylrhodamine (TAMRA) which may be attached to any T position or at the 3' end thereof as described in Livak et al., Guidelines for Designing TaqMan™ Fluorogenic Probes for 5' Nuclease Assays, In" Perkin-Elmer Research News, 1995, Applied Biosystems Division of Foster City, Calif., the content of which is incorporated herein by reference. Preferably, the probe may be adapted to have a higher melt temperature ($T_m$) than the primers, and during the extension phase, the probe is at least substantially hybridized to the target nucleic acid sequence.

It will be understood that based on this disclosure that the present invention is not limited to this particular reporter-quencher pair or the particular linkages used to attach the molecules to the probe. Rather, as previously discussed herein, a range of reporter-quencher pairs may be attached to the nucleic acid probe through various linkages as known to the skilled artisan. Further, the reporter-quencher pair need not be located on nucleotides which are immediately adjacent, instead, the quencher may be attached to any nucleotide on the probe and still quench the emission of the reporter attached to the 5' end thereof.

In one preferred embodiment, amplification of the target nucleic acid sequence may be detected by measuring the fluorescence of the reaction mixture in the presence of a thermostable intercalating fluorescent dye such as ethidium bromide (RtBr), or SYBR green 1 available from Qualicon, Wilmington, Del. The fluorescence detects the formation of any double-stranded DNA and is an indication that the target sequence specified by the primer pair has been produced.

There are many linking moieties and methodologies for attaching reporters and quenchers to the 5' or 3' termini of oligonucleotides as known in the art. Preferably, commercially available linking moieties are employed that can be attached to an oligonucleotide during synthesis. Suitable moieties are available from Clontech Laboratories of Palo Alto, Calif.

Rhodamine and fluorescein dyes may be conveniently attached to the 5' hydroxyl of an oligonucleotide at the conclusion of solid phase synthesis by way of dyes derivatized with a phosphoramidite moiety as known in the art.

It will be understood that the invention is not limited to the release of a reporter from the nucleic acid probe in order to cause fluorescence of a sample as the target DNA is amplified. Rather, one skilled in the art would recognize that other techniques for detecting amplification as known in the art may also be used. For example, techniques such as PCR-based quantitative sequence detection (QSD) may be performed using nucleic acid probes which, when present in the single-stranded state in solution, are configured such that the reporter and quencher are sufficiently close to substantially quench the reporter's emission. However, upon hybridization of the intact reporter-quencher nucleic acid probe with the amplified target nucleic acid sequence, the reporters and quenchers become sufficiently distant from each other. AS a result, the quenching is substantially abated causing an increase in the fluorescence emission detected.

The method of the present invention may include differential quenching of the reporter due to the interaction of the reporter-quencher probe with the amplified target nucleic acid sequence. The precise mechanism by which the reporter-quenchers are brought together or taken apart may vary. Guidelines for designing, producing and using suitable reporter-quencher nucleic acid probes are known in the art and are described in the above-cited references including, for example, Liak et al., supra.

The 3' terminal nucleotide of the nucleic acid probe may be rendered incapable of extension by a nucleic acid polymerase in one embodiment of the invention. Such blocking may be carried out by the attachment of a fluorescer or quencher molecule to the terminal 3' carbon of the nucleic acid probe by a linking moiety, or by making the 3'-terminal nucleotide a dideoxynucleotide. Alternatively, the 3' end of the nucleic acid probe may be rendered impervious to the 3' to 5' extension activity of a polymerase by incorporating one or more modified internucleotide linkages onto the 3' end of the oligonucleotide. Minimally, the 3' terminal internucleotide linkage must be modified, however, additional the internucleotide linkages may be modified. It is preferred that the 5' to 3' exonuclease ability of the DNA polymerase to cleave off the 5' nucleotide to which the fluorescer molecule is attached is preserved.

Internucleotide modifications which prevent elongation from the 3' end of the nucleic acid probe and/or which block the 3' to 5' exonuclease activity of the DNA polymerase during PCR may include phosphorothioate linkages, methylphosphonate linkages, boranophosphate linkages, and other similar polymerase-resistant internucleotide linkages. An alternative method to block 3' extension of the probe is to form an adduct at the 3' end of the probe using mitomycin C or other like antitumor antibiotics such as those of Basu et al., 1993, Biochemistry 32:4708-4718). Thus, the precise mechanism by which the 3' end of the nucleic acid probe is protected from cleavage is not essential so long as the quencher molecule is not cleaved from the nucleic acid probe.

The level of fluorescence is preferably measured using a laser/fluorometer such as, for example, an ABI Prism Model 7900 Sequence Detector or a BAX™ fluorometer. However, similar detection systems for measuring the level of fluorescence in a sample are included in the invention.

In a preferred embodiment, amplification of a specific target sequence specified by the primer pair is detected by QSD. Preferably, a Model 7900 Sequence Detector laser fluorometer/thermal cycler is used for the QSD procedure to detect the fluorescence of the PCR sample mixture before and after each round of amplification. Such a QSD procedure is described in Heid et al. (1996, Genome Res. 6:986-994), the content of which is incorporated herein by reference.

QSD is similar to standard PCR assays in that DNA is used as a DNA template to generate millions of copies of the target DNA by *Thermus aquaticus* (Taq) DNA polymerase enzyme and thermal cycling. However, QSD differs significantly from PCR in that QSD involves the detection of the hybridization of a nonextendible internal fluorogenic reporter-quencher DNA probe (e.g., a TaqMan™ probe available from Perkin Elmer which contains a reporter at one end and a quencher on the other end and which is specific for the target DNA sequence being amplified as described in Heid et al. (1996, Genome Res. 6:986-994). When the probe is intact, fluorescent energy transfer occurs and the reporter dye fluorescence is absorbed by the quenching dye (id. at 987). During the extension phase of the PCR cycle, the fluorescent hybridization probe is cleaved by the 5' to 3' exonuclease activity of the DNA polymerase. Once the probe is cleaved, the reporter dye emission is no longer quenched resulting in an increase of the reporter dye fluorescence emission spectra after each round of replication.

The present invention also includes a kit for determining the presence of staphylococcal enterotoxin A in a sample. The kit comprises at least one primer pair, each of which is capable of amplifying a unique target nucleic acid of a gene [SEQ ID NO: 8] encoding staphylococcal enterotoxin A. In a preferred embodiment, the target nucleic acid is the nucleic acid sequence [SEQ ID NO:7] wherein the forward and reverse primer pairs are selected from [SEQ ID NO:3] and [SEQ ID NO:5] and [SEQ ID NO:4] and [SEQ ID NO:6], respectively. In another preferred embodiment, the nucleic acid probe used to detect the amplification product has a nucleic acid sequence selected from [SEQ ID NO:1] and [SEQ ID NO:2]. However, the present invention is not limited to these primers or nucleic acid probe sequences. Rather, any nucleic acid probe having a sequence between two primers spanning from nucleotide residue 241 up to and including nucleotide residue 841 of the staphylococcal enterotoxin A gene [SEQ ID NO: 8] is encompassed in the invention.

The kit is used pursuant to the methods disclosed in the invention. Further, the kit may be used in standard PCR, or in a homogeneous format PCR procedure as known in the art. One skilled in the art would appreciate based on the disclosure herein that the kit may used in any of the aforementioned procedures and in any combination thereof.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

What is claimed is:

1. A method of determining the presence of staphylococcal enterotoxin A gene in a sample, comprising:

contacting a target nucleic acid sequence which comprises a portion of the *S. aureus* entA gene encoding staphylococcal enterotoxin A, with polymerase chain reaction reagents specific for the target nucleic acid sequence, the polymerase chain reaction reagents including a primer selected from the group consisting of a forward primer consisting of a specific sequence selected from the group consisting of SEQ ID NO: 3, SEQ ID NO: 4 and combinations thereof, and a reverse primer consisting of a specific sequence selected from the group consisting of SEQ ID NO: 5, SEQ ID NO: 6 and combinations thereof, a polymerase enzyme, and a nucleic acid probe, wherein the nucleic acid probe further comprises:

a nucleic acid sequence that hybridizes to a portion of the target nucleic acid sequence wherein the portion is unique to the nucleic acid encoding staphylococcal enterotoxin A, and wherein the nucleic acid sequence of the nucleic acid probe is selected from the group consisting of SEQ ID NO: 1, SEQ ID NO: 2 and combinations thereof;

a reporter attached to a 5' end of the nucleic acid probe, said reporter capable of emitting a detectable signal;

a quencher attached to a 3' end of the nucleic acid probe capable of substantially quenching the reporter and prevent emission of the detectable signal, when the nucleic acid probe is intact, wherein the reporter becomes substantially unquenched when the nucleic acid probe is cleaved by the polymerase enzyme during amplification of the target nucleic acid sequence;

amplifying the target nucleic acid sequence by thermal cycling, wherein the thermal cycling will amplify the target nucleic acid sequence; and measuring the level of fluorescence in the sample subsequent to thermal cycling, and further wherein the level of detectable signal is correlated to an amount of the nucleic acid encoding staphylococcal enterotoxin A in the sample, thereby quantitatively detecting the nucleic acid encoding staphylococcal enterotoxin A in the sample.

2. The method of claim 1, wherein the reporter is selected from the group consisting of 1-dimethylaminonaphthyl-5 sulfonate, 1-anilino-8-naphthalene sulfonate, 2-p-touidinyl-6-naphthalene sulfonate, 3-phenyl-7-isocyanatocoumarin, 9-isothiocyanatocacridine, N-(p-(2-benzoxazolyl)phenyl)

maleimide, benzoxadiazoles, stilbenes, pyrenes, 6-carboxyfluorescein, tetrachloro-6-carboxyfluorescein, 2,7-dimethoxy-4,5-dichloro-6-carboxyfluorescein, hexachloro-6-carboxyfluorescein, 5-carboxyfluorescein, 6-carboxy-2',4,7,7'-tetrachlorofluorescein, carboxy-X-rhodamine and 6-carboxy-4',5'-dichloro-2',7'-dimethoxyfluorescein.

3. The method of claim 1, wherein the quencher is selected from the group consisting of 6-carboxytetramethylrhodamine, tetramethylrhodamine and 4-(4-dimethylaminophenylazo) benzoic acid.

* * * * *

SEQUENCE LISTING

```
<160> NUMBER OF SEQ ID NOS: 8

<210> SEQ ID NO 1
<211> LENGTH: 36
<212> TYPE: DNA
<213> ORGANISM: Artificial Sequence
<220> FEATURE:
<223> OTHER INFORMATION: Probe 1

<400> SEQUENCE: 1 c acttgtaaat ggtagcgaga aaagcgaaga aataa                          36

<210> SEQ ID NO 2
<211> LENGTH: 37
<212> TYPE: DNA
<213> ORGANISM: Artificial Sequence
<220> FEATURE:
<223> OTHER INFORMATION: Probe 2

<400> SEQUENCE: 2 acagtacct ttggaaacgg ttaaaacgaa taagaaaa                          37

<210> SEQ ID NO 3
<211> LENGTH: 20
<212> TYPE: DNA
<213> ORGANISM: Artificial Sequence
<220> FEATURE:
<223> OTHER INFORMATION: Forward primer 1

<400> SEQUENCE: 3
```

```
tgcc ctaacgtgga caacaa                                              20

<210> SEQ ID NO 4
<211> LENGTH: 23
<212> TYPE: DNA
<213> ORGANISM: Artificial Sequence
<220> FEATURE:
<223> OTHER INFORMATION: Forward primer 2

<400> SEQUENCE: 4 caattta tggctagacg gtaaac                                           23

<210> SEQ ID NO 5
<211> LENGTH: 21
<212> TYPE: DNA
<213> ORGANISM: Artificial Sequence
<220> FEATURE:
<223> OTHER INFORMATION: Reverse primer 1

<400> SEQUENCE: 5 ctgctcc ctgcaattca gact                                             21

<210> SEQ ID NO 6
<211> LENGTH: 21
<212> TYPE: DNA
<213> ORGANISM: Artificial Sequence
<220> FEATURE:
<223> OTHER INFORMATION: Reverse Primer 2

<400> SEQUENCE: 6 ct tgcttgaaga tccaactcc                                             21

<210> SEQ ID NO 7
<211> LENGTH: 600
<212> TYPE: DNA
<213> ORGANISM: Staphylococcus aureus

<400> SEQUENCE: 7
tatgctttag aggtgagcaa aatgaaaaaa acagcattta tactactttt attcattgcc    60
ctaacgtgga caacaagtcc acttgtaaat ggtagcgaga aaagcgaaga aataaatgaa   120
aaagatttgc gaaaaagtc tgaattgcag ggagcagctt taggcaatct taaacaaatc   180
tattattaca atgaaaaagc taaaactgaa aataaagaga gtcacgatca attttttacag  240 catactatat tgtttaaagg cttttttaca aatcattcat ggtataacga tttattagta   300
gattttgatt caaaggatat tgttgataaa tataaaggga aaaaagtaga cttatatggt   360
gcttattatg gttatcaatg tgcgggtggt acaccaaaca aaacagcttg catgtatggt   420
ggtgtaacgt tacatgataa taatcgattg accgaagaga aaaaagtgcc gatcaattta   480
tggctagacg gtaaacaaaa tacagtacct ttggaaacgg ttaaaacgaa taagaaaaat   540
gtaactgttc aggagttgga tcttcaagca agacgttatt tacaggaaaa atataattta   600

<210> SEQ ID NO 8
<211> LENGTH: 1443
<212> TYPE: DNA
<213> ORGANISM: Staphylococcus aureus entA gene

<400> SEQUENCE: 8
ccaaaataat ggcaagtact ccgttgtcaa taccaagtaa gtaagatatc tgaaatgtat    60
aatagagtaa aaatgaaatc tttttattat attatagaca agtataaaaa aggtatagta   120
```

-continued

```
atatatgtat gtataagtaa ataatgataa ttctataatt attgtatata actaataatt      180
acttcgacaa aaataatcta ttatccaaat attttagata ataaaaagtt tgtatggaat      240
tatgctttag aggtgagcaa aatgaaaaaa acagcattta tactactttt attcattgcc      300
ctaacgtgga caacaagtcc acttgtaaat ggtagcgaga aaagcgaaga aataaatgaa      360
aaagatttgc gaaaaaagtc tgaattgcag ggagcagctt taggcaatct taaacaaatc      420
tattattaca atgaaaaagc taaaactgaa aataaagaga gtcacgatca atttttacag      480
catactatat tgtttaaagg ctttttttaca aatcattcat ggtataacga tttattagta     540
gattttgatt caaaggatat tgttgataaa tataaaggga aaaaagtaga cttatatggt      600
gcttattatg gttatcaatg tgcgggtggt acaccaaaca aaacagcttg catgtatggt      660
ggtgtaacgt tacatgataa taatcgattg accgaagaga aaaaagtgcc gatcaattta      720
tggctagacg gtaaacaaaa tacagtacct ttggaaacgg ttaaaacgaa taagaaaaat      780
gtaactgttc aggagttgga tcttcaagca agacgttatt tacaggaaaa atataattta     840
tataactctg atgtttttga tgggaaggtt cagagggggat taatcgtgtt tcatacttct     900
acagaacctt cggttaatta cgatttattt ggtgctcaag gacagaattc aaatacacta    960
ttaagaatat atagagataa taaaacgatt aactctgaaa acatgcatat tgatatatat    1020
ttatatacaa gttaaacatg gtagttttga acacgtaatg ttcagattat tatgaaccga    1080
gaataatctg aaagtttaca agcagtaaaa aaagtatatg tgctataata tgctttgagc    1140
aagttggata gatggtggct atctgagtat aaggaggtgg tgcctatggt ggcattactg    1200
aaatctttag aaaggagacg cctaatgatt acaattagta ccaatgttgc agtttggttt    1260
attccttatt gcattgatag gtctagtaat caagcttatt gaattaagca ataaaaaata    1320
accatcgcta actttggctg gtttcgatgg ttaaatggtt attaatttaa tctttaatct    1380
aaaatagcca ccgtcttttt aacgggctca ttagggtaac atgtttgcgc atgttgccct    1440
ttt                                                                  1443
```